United States Patent [19]

Gindrat et al.

[11] Patent Number: 5,041,290
[45] Date of Patent: Aug. 20, 1991

[54] METHOD OF PROTECTING USEFUL PLANTS FROM DISEASES CAUSED BY SOIL-BORNE AND SEED-BORNE PATHOGENS BY TREATING SEEDS WITH CULTURES OF MICROORGANISMS

[75] Inventors: Daniel Gindrat, Bassins, Switzerland; Daniel Walther, Gainesville, Fla.

[73] Assignee: Ciba-Geigy Corporation, Ardsley, N.Y.

[21] Appl. No.: 353,150

[22] Filed: May 15, 1989

Related U.S. Application Data

[63] Continuation of Ser. No. 258,102, Oct. 13, 1988, abandoned, which is a continuation of Ser. No. 912,897, Sep. 26, 1986, abandoned.

[30] Foreign Application Priority Data

Oct. 2, 1985 [CH] Switzerland .......................... 4252/85
Feb. 3, 1986 [CH] Switzerland ............................ 398/86

[51] Int. Cl.$^5$ ...................... A01N 63/00; C12N 1/14; A01) 1/06
[52] U.S. Cl. ...................................... 424/93; 435/254; 435/911; 47/57.6; 47/DIG. 9; 71/3
[58] Field of Search .................. 424/93; 435/254, 911; 71/3; 47/58, 57.6, DIG. 9

[56] References Cited

FOREIGN PATENT DOCUMENTS 272266 1/1964 Australia ............................. 424/93
28697/77 3/1979 Australia ............................. 424/93
61687/86 2/1987 Australia ............................. 424/93

OTHER PUBLICATIONS

Hubbard, et al., 1982, Can. J. Microbiol., 28:431–437.
Veseley et al., 1984, Zentrablatt Mikrobiol., 139:257–265.
Y. Elad et al., *Plant Soil*, 66, 279–281 (1982).
D. Gindrat et al, in "Soil-Borne Plant Pathogens", pp. 537–551; Ed. B. Schippers & Gams; Academic Press (1979).
D. Vesley, *Phytopathology Z*, 90, 113–115 (1977).
D. Vesley, in Soil-Borne Plant Pathogens, pp. 593–599, Ed. B. Schippers & W. Gams; Academic Press (1979).
D. Vesley et al, *Zentralblatt Mikrobiol.*, 139, 257–265 (1984).
C. C. Heye et al, *Phytopathology*, 73, 650–654 (1983).
J. P. Hubbard et al, *Can. J. Microbio.*, 28, 431–437 (1982).
M. Tweit et al., *Phytopathology*, 44, 686–694 (1954).
I. Chang et al, *Phytopathology*, 58, 1395–1401 (1968).
M. Tweit et al., *Ann. App. Biol.*, 43, 538–552 (1955).
T. Kommmedahl et al, *Phytopathology*, 65, 296–300 (1975).
G. E. Harman et al., Phytopathology, 70, 1167–1172 (1980).
G. E. Harman et al., Ann. Appl. Biology, 90, 1–6 (1978).
M. L. Handoo et al., Seed Research, 1, 151–156 (1979).

*Primary Examiner*—Elizabeth C. Weimar
*Assistant Examiner*—David T. Fox
*Attorney, Agent, or Firm*—George R. Dohmann; Edward McC. Roberts

[57] ABSTRACT

Useful plants can be protected against soil-borne and seed-borne diseases by coating the seeds of said plants with fungus spores, in particular ascospores of *Chaetomium globosum*, mycelium, bacteria or culture extracts thereof. The protection is in some cases superior to that afforded by sugar beet and cotton seeds which are coated with commercially available fungicides.

2 Claims, No Drawings

METHOD OF PROTECTING USEFUL PLANTS FROM DISEASES CAUSED BY SOIL-BORNE AND SEED-BORNE PATHOGENS BY TREATING SEEDS WITH CULTURES OF MICROORGANISMS

This application is a continuation of application Ser. No. 258,102, filed 10/13/88, now abandoned, which is a continuation of application Ser. No. 912,897, filed 9/26/86, now abandoned.

The present invention relates to a method of protecting useful plants, especially sugar beet and cotton plants, from diseases caused by soil-borne as well as seed-borne microorganisms. The method comprises providing the seeds with a protective coating which contains an effective amount of fungus spores, in particular ascospores of *Chaetomium globosum*, mycelium, bacteria or culture extracts thereof. The invention also relates to the seeds coated with *Chaetomium globosum* ascopores, and to a process for the preparation thereof.

Seeds shall be understood in the context of this invention as meaning in particular the parts of plants necessary for propagation, for example grains, seeds, tubers, cuttings and shoots.

The germinating plantlet is often attacked by soil-borne pathogenic microorganisms that cause the plants to rot and die, whereby severe damage is caused to agriculture. Such pathogens are normally controlled with chemical fungicides.

Attempts have also been made to use microorganisms themselves to protect plants against attack by pathogens. Interesting as such attempts have been, suitable methods have been unable to gain acceptance in actual practice because industrially produced fungicides have proved more effective and easier to handle.

The present invention is based on the surprising observation that it has been possible in in vitro and in field tests to match and even surpass the protective action of seeds of useful plants, especially of sugar beet and cotton, coated with commercially available fungicides by dressing seeds with a coating that contains ascospores of *Chaetomium globosum*. The spores used are simple to culture and are not more susceptible to drying out than the seeds coated therewith. The spores can be mixed in simple manner with a seed dressing. They are also no more difficult to handle than a chemical fungicide. The spores can be cultured and harvested using simple equipment and with little effort.

Sugar beet plants (*Beta vulgaris*) are attacked in the soil by a variety of microorganisms, among which the most important are pathogenic fungi such as *Pythium ultimum, Rhizoctonia solani, Aphanomyces cochlioides, Phoma betae*, Fusarium sp., and Botrytis sp.. These pathogens infect the tissues of the roots and stalk, resulting in breakage and, ultimately, in rot of the plantlet.

The sugar beet seeds are flat, pentagonal stars which tend to become entangled with one another. For trouble-free mechanical sowing, they are coated and pelleted by the seed dealer. The seed coating routinely contains a chemical fungicide or mixture of fungicides.

Cotton plants (*Gossypium hirsutum*) are likewise infected by the fungi *Pythium ultimum* and *Rhizoctonia solani*, along with *Thielaviopsis basicola* and Fusarium spp. These are usually large-scale crops which are intensively treated with agrochemicals, as diseases and crop losses result in financial loss that cannot be compensated for by yields of other crops. The treatment of the crop and/or of the seeds with fungicides is a routine matter in cotton growing.

*Chaetomium globosum* belongs to the fungi of the class Ascomycetes. It is the most widespread species of Chaetomium. The fungus is found in the soil and, in particular, in the root zone of different plants. It is a cellulose saprophyte which is found on plant residues. The ability to degrade cellulose and other polysaccharides has been studied but not utilised technically.

The use of *Chaetomium globosum* for controlling plant pathogens has been described in other contexts. Thus, for example, Tveit and Wood have described the control of *Fusarium nivale* blight in oats in Ann. appln. Biol. 43, 538–552 (1955); and the control of corn root infection caused by *Fusarium roseum* has been described by Chang and Kommedahl in Phytopathology 58, 1395–1401 (1968) and by Kommedahl and Mew in Phytopathology 65, 296–300 (1975). Finally, Heye and Andrews describe the control of apple scab caused by *Venturia inaequalis* in Phytopathology 73, 650–654 (1983).

The successful use of *Chaetomium globosum* for protecting seeds of sugar beet and cotton is novel.

*Chaetomium globosum* can be readily cultivated even at room temperature in a malt or cellulose-containing culture medium that contains trace elements in a neutral to acid pH range.

The mycelium forms rapidly as a tissue mat that adheres to a solid culture medium or, if it has been cultured on a filter paper placed on the culture medium, also adheres to a filter paper culture. The perithecia that contain ascospores then form on the hyphae and impart a black colour to the substrate. A mycelium that carries no perithecia forms in liquid shake cultures. On the filter paper cultures, the perithecia are isolated by scraping them off the filter paper and they are then dried and processed by grinding them to a powder that consists chiefly of free ascospores and mycelium and perithecia fragments. In liquid cultures, the mycelium is isolated by filtering the medium and the isolate is then comminuted in a high-speed rotary propeller mill.

The resultant powder consisting of ascospores and pieces of hyphae is stable and can be stored in the temperature range from 10° to 30° and at a relative humidity from 20 to 60%. Even spores that are stored for some considerable time germinate within hours when they come in contact with moist soil and/or a nutrient medium.

The seeds of useful plants are wetted in known manner with a liquid coating material that can be dried. Then, during the drying procedure when they are still tacky, the seeds are contacted with the ascospore powder, e.g. by shaking or rolling the seeds over a layer of powder which has been applied to a surface and finally dried until the coat is completely dry.

Coating compositions for the seed dressing are suitable solutions. These solutions may contain water or an organic solvent, and the material forming the protective coat may be organic or inorganic. Typical examples of such solutions are:

18 parts of polyurethane prepolymer containing free isocyanate end groups (No. W. 23 091, Pittsburg Plate Glass Co.)
9 parts of polyketimine (No. W. 23 092, Pittsburg Plate Glass Co.)
73 parts of acetone 50 parts of a high molecular polyvinyl acetate homopolymer (S-6930, H. B. Fuller Co.)
20 parts of water 1-2 parts of methyl cellulose
200 parts of water 1-2 parts of xanthane
100 parts of water 15-30 parts of gum arabic
100 parts of water.

Coating compositions containing clay particles, alginates and further formulation substances are also employed.

The seeds are moistened or sprayed with the solutions and then dried in a stream of air on a sieve or in a fluidised bed drier and dusted while still tacky with the ascospore powder. The number of spores applied to each plant should be $1.5\times10^5$ to $6\times10^5$ to be fully effective. The spore density is determined by dissolving a number of seeds in water and analysing the suspension with a colorimeter or a hematometer.

The seeds coated with the spores can be stored just as well as untreated seeds. During germination they are protected against infections caused by soil-borne pathogens.

The culturing of *Chaetomium globosum* and the harvesting of the ascospores is extremely simple and can be effected without technical aids even on a small scale. This can be of particular interest whenever the use of chemical fungicides is dispensed with for one reason or another.

*Chaetomium globosum* grows virtually everywhere that cellulose or polysaccharides and moisture are available to it. Culturing was possible in different culture media and in the temperature range from 10°-30° C. Examples of liquid and solid culture media are:

2 parts of malt extract (Oxoid) (adjusted to pH 5.3)
100 parts of water
(culturing for 4 days at 24° C. with slow speed stirrer).

1 part of glucose
0.3 part or yeast extract (Difco)
2 parts of agar (Sigfried)
100 parts of water 1 part of cellulose (Merck, microcrystalline)
2 parts of agar
0.3 part of yeast extract (Difco)
100 parts of water 1 g of $KH_2PO_4$ (Czapel-Dox)
0.5 g of $MgSO_4$
0.5 g of KCl
2 g of $NaNO_3$
0.1 g of $FeSO_4$
20 g of glucose
water to make up 1 liter 2 parts of malt extract (Oxoid)
2 parts of agar (Sigfried)
100 parts of water 1 g of $KH_2PO_4$
0.5 g of $MgSO_4$
2 g of $KNO_3$
2 g of $CaCO_3$
20 g of glucose
0.1 g of yeast extract
12 g of malt extract (corn steep liquor)
water to make up 1 liter The mycelium which is densely populated with perithecia is decanted or isolated from the culture after 4-6 weeks and dried.

The culture of ascospores is also obtained by soaking filter paper with a suspension containing $10^4$-$10^5$ spores per ml in a culture broth and then culturing in the temperature range from 10°-25° C. in a petri dish at relatively high humidity. After about 4 weeks the filter papers are dried and the fungal biomass can be scraped off with a spatula.

The invention is illustrated by the following non-limitative Examples.

EXAMPLE 1

Culturing Ascospores of *Chaetomium globosum*

Petri dishes, to each of which has been added a filter paper as source of cellulose, are half-filled with a nutrient solution consisting of malt (2%)-agar (2%). The nutrient solution is then inoculated with a few drops of a suspension of soil infected with *Chaetomium globosum*. The petri dishes are kept in climatic chambers at 22° C. A mycelium forms on the culture, followed after about 10 days by the formation of perithecia which are visible as black dots on the mycelium. After 4 weeks, a number of perithecia are removed from the culture and processed to a suspension which contains $10^4$-$10^5$ ascospores per ml. Filter papers are then soaked with this suspension, placed on malt extract nutrient media in petri dishes and cultured for 4-6 weeks at 22° C. in a climatic chamber. The filter papers are overgrown during this time with mycelium and perithecia. The filter papers are dried and the mycelia and spores are scraped off with a spatula and the fungal biomass is ground or comminuted in a mixer at 500 rpm, to give a dark powder consisting of spores and fragments of hyphae that is suitable for seed coating.

A round filter paper of 8.7 cm diameter yields on average 120 mg of powder consisting of $10^8$-$10^9$ ascospores and fragments of hyphae.

EXAMPLE 2

Coating Sugar Beet Seeds with a Layer of Ascospores of *Chaetomium globosum*

Adhesive solutions are prepared consisting of

| | | |
|---|---|---|
| methyl cellulose | 0.5 part | 1 part |
| gum arabic | 15.0 parts | 30 parts | water to make up 100 parts by volume.

These solutions are sterilised for 20 minutes in an autoclave at 120° C. and then blown through a jet into the air stream of a fluidised bed drier containing sugar beet seeds. 0.7 ml of solution is applied to 3.2 g of seeds (c. 260 seeds). The seeds provided with a tacky coating are then shaken together with the ascospore powder, sieved and dried on the sieve. Each seed is coated with 150,000 to 600,000 spores. Measurement is made by suspending 10 seeds in 10 ml of water and determining from the suspension the number of spores contained therein with a hematometer.

EXAMPLE 3

Coating Cotton Seeds with a Layer of Ascospores of *Chaetomium globosum*

10 g of cotton seeds (c. 110 seeds) are sprayed in a fluidised bed drier with 0.5 ml of a 0.6% solution of methyl cellosolve and the still tacky seeds are then rolled in a petri dish over an ascospore powder and then dried on a sieve.

EXAMPLE 4

Coating Sugar Beet Seeds with a Mycelium of *Chaetomium globosum*

A 250 ml Erlenmeyer flask is charged with 150 of a 2% malt extract (Oxoid) and this nutrient solution is inoculated with 1 ml of a spore suspension containing $10^5$ ascospores per ml. The culture is incubated for 4 days at 24° C.

Then 10 ml of the oily culture broth is removed and 1.6 g of sugar beet seeds are added thereto. Seeds and broth are mixed for 10 minutes at room temperature and the seeds are then allowed to drip on a sieve. The treated seeds are sown while still moist.

EXAMPLE 5

Coating Sugar Beet Seeds with Iron Phosphate and Ascospores of *Chaetomium globosum*

3.2 g of sugar beet seeds are stirred at room temperature for 20 minutes in a filtered solution of 1.36 g of iron phosphate in 20 ml of a 0.36 molar solution of oxalic acid of pH 5.4. The seeds are poured onto a sieve and dried in a stream of air. After they have been dried, the seeds are coated with ascospores as described in Example 2.

EXAMPLE 6

Coating Seeds with Chemical Fungicide 6.4 g of seeds or 10 g of cotton seeds are stirred for 20 minutes at room temperature in 20 ml of a 0.1% solution of 3α,4,7,7α-tetrahydro-2-[(trichloromethyl)thio]-1H-isoindole-1,3(2H)-dione (Captan, prepared by dissolving in 0.2% Orthozid 50, Sigfried). The seeds are then collected on a sieve and dried in a stream of air.

EXAMPLE 7

Germination Assays with Ascospores of *Chaetomium globosum*

The germination capacity of stored spores encapsulated in seed coats was compared with that of freshly harvested spores.

Spores which have been freshly harvested from cultures and samples of spores that have been stored for 1 to 15 months at 10°-30° C. and 20-60% relative humidity are placed on agar plates and examined in climatic chambers at 22° C. for their germination capacity.

Almost all spores examined germinated within 7 hours, in time to be able to protect the germinating seeds.

| Temperature during storage (°C.) | Germination capacity after storage for | | | | |
|---|---|---|---|---|---|
| | no storage (fresh spores) | 1 month | 5 months | 10 months | 15 months |
| 10° | — | 84% | 85% | 90% | 90% |
| 15° | — | 78% | 80% | 59% | 13% |
| 20° | 50% | 81% | 91% | 86% | 92% |
| 25° | — | 78% | 90% | 89% | 91% |
| 30° | — | 76% | 85% | 82% | 85% |

EXAMPLE 8

Assay for Germination Capacity of Coated Seeds

Untreated as well as chemically treated sugar beet and cotton seeds are put into petri dishes (10 seeds per dish) on a thick layer of moist filter paper. The petri dishes are then put into a climatic chamber and kept under observation. The criterion for germination is the formation of roots.

The sugar beet seeds are kept for 12 hours in daylight at 20° C. and 12 hours in the dark at 14° C. and at 80-90% relative humidity. Germination of the untreated seeds is 75% between the 3rd and 8th day and up to 90% on the 20th day. The treated seeds begin to germinate later after the 6th day and likewise achieve up to 85% germination by the 20th day.

The cotton seeds are kept for 14 hours in daylight at 25° C. and 10 hours in the dark at 20° C. Germination of the untreated seeds is almost 100% between the 2nd and 8th day. Germination of the treated seeds is more than 90%.

EXAMPLE 9

Assay for the Protective Action of Sugar Beet Seeds Coated with Ascospores of *Chaetomium globosum* in a Climatic Chamber Untreated sugar beet seeds and seeds coated with ascospores as described in Example 2 are put into plastic dishes measuring 10×12×4.5 cm and filled with soil. 20 seeds are sown in each dish, with each seed being sown individually into a 9 mm cavity made in the soil. The soil is disinfected (100° C.) soil and soil which has been inoculated with *Pythium ultimun* and *Rhizoctonia solani*. The seed dishes are then kept in climatic chambers for 12 hours in daylight at 20° C. and 12 hours in the dark at 14° C. and 80-90% relative humidity. The seed dishes filled with infected soil are prepared in the climatic chamber 3 days before sowing. Five dishes each containing 100 seeds are used per assay. The dishes are kept under daily observation and the perished plants are removed and used for mycological investigation of the pathogens.

The assay is terminated 3 weeks before sowing and the number and condition of the plantlets is determined.

The results are as follows:

| Seeds | Surviving plants | | |
|---|---|---|---|
| | Soil disinfected | inoculated with | |
| | | *Pythium ultimum* | *Rhizoctonia solani* |
| untreated | 79% | 18% | 7% |
| treated with *Chaetomium globosum* 1.5 · 10⁵ spores according to Example 2 | — | 63% | 68% |
| treated with 0.1% of Captan | — | 88% | 53% |

-continued

| Seeds | Surviving plants | | |
|---|---|---|---|
| | Soil disinfected | inoculated with Pythium ultimum | Rhizoctonia solani |
| according to Example 6 | | | |

EXAMPLE 10

Assay for Determining the Protective Action of Cotton Seeds Coated with Ascospores of *Chaetomium globosum* in a Climatic Chamber Plastic dishes measuring 10×12×4.5 cm are filled with soil inoculated with *Pythium ultimum* and *Rhizoctonia solani* and kept for 3 days in a climatic chamber at 80-90% relative humidity for 16 hours in daylight at 26° C. and 8 hours in the dark at 20° C. Then 9 cotton seeds are sown in each dish in a 15 mm cavity made in the soil. 10 dishes or 90 seeds are used for each assay. The dishes are kept under regular observation and the perished plants are removed and used for mycological investigation of the pathogens. The assay is terminated after 3 weeks and the number and condition of the germinated plantlets (in %) is determined.

| Seeds | Surviving plants | | |
|---|---|---|---|
| | Soil disinfected | inoculated with Pythium ultimum | Rhizoctonia solani |
| untreated | 76% | 16% | 20% |
| treated with *Chaetomium globosum* 1.5 · 10⁵ spores according to Example 2 | — | 76% | 58% |
| treated with 0.1% of Captan according to Example 6 | — | 84% | 40% |

EXAMPLE 11

Protective action of sugar beets provided with different protective coatings

Sugar beet seeds are coated according to the method of Example 2 with different adhesive solutions and coated with ascospore powder. The spore density was only 1.5·10⁵ spores per seed. The seeds are compared with untreated seeds and with seeds treated with Captan (cf. Example 6).

Seed dishes are filled with soil which is naturally infected with *Pythium ultimum*. Then 20 sugar beet seeds are sown in each seed dish to a depth of 9 mm and the dishes are left in the climatic chamber under the same conditions and with regular watering. The germination of the seeds is monitored and perished plants are removed. The activity of the protective coating is evaluated 28 days after sowing by counting the number of surviving plants.

| Seed coating | Surviving plants | |
|---|---|---|
| | in disinfected soil | soil infected with Pythium ultimum |
| none | 91% | 51% |
| 0.5% methyl cellulose + 1.5 · 10⁵ spores | | 72% |
| 1% methyl cellulose + 1.5 · 10⁵ spores | | 75% |
| xanthane 0.3% + 1.5 · 10⁵ spores | | 65% |
| xanthane 1% + 1.5 · 10⁵ spores | | 73% |
| gum arabic 13% + 1.5 · 10⁵ spores | | 66% |
| gum arabic 30% + 1.5 · 10⁵ spores | | 77% |
| none | 9% | |
| mycelium culture (Example 4) | | 57% |
| Captan, 0.1% | | 86% |

The same assay was carried out with soil inoculated with *Pythium ultimum*. The seeds were untreated, coated with 1.5·10⁵ ascospores of *Chaetomium globosum* according to Example 2, with iron phosphate and ascospores according to Example 5, or with Captan according to Example 6.

| Seed coating | Surviving plants | |
|---|---|---|
| | disinfected soil | soil inoculated with Pythium ultimum |
| none | 86% | 9% |
| 0.5% methyl cellulose + 1.5 · 10⁵ ascospores | — | 48% |
| iron phosphate + 0.5% meth.cell. + 1.5 · 10⁵ ascospores | — | 67% |
| Captan 0.1% | — | 88% |

EXAMPLE 12

Field Test

Sugar beet seeds were sown in April with a mechanical sower in a field in Corcelles, Switzerland. The plants were counted after 36 days and evaluated. Each seed coating was tested in 6 test plots of one row of 12 m.

The plots were biologically examined and the following pathogenic microorganism were observed.: *Aphanomycetes cochlioides*, *Rhizoctonia* spp., *Fusarium* spp., *Pythium debarynum*.

Untreated seeds and seeds coated with spores of *Chaetomium ultimum* according to Example 2 or seeds coated industrially with Thiram* (TMTD) were used for the test. The surviving plants were counted after 35 days.

| Seed coating | Surviving plants | |
|---|---|---|
| | Chavorney | Corcelles |
| none | 42% | 55% |
| according to Example 2 with 1.5 · 10⁵ ascospores | 64% | 61% |
| industrially without fungicide | 32% | 37% |
| industrially with TMTD* | 41% | 43% |

*Thiram or TMTD, tetramethylthiuram disulfide $(CH_3)_2N-CS-S-S-C-S-N(CH_3)_2$, IG Bayer. The treated seeds were obtained from Kleinwanzlebener Saatzucht in Einbeck, Germany.

What is claimed is:

1. A method for protecting emerging sugar beet seeds and seedlings against damping off disease caused by pathogenic soil-borne and seed-borne fungi selected from the genera consisting of Pythium, Rhizoctonia, Fusarium, and Aphanomyces, which method comprises seed treatment with an effective amount of ascospores of *Chaetomium globosum*.

2. A method according to claim 1, wherein the protective coating contains an effective amount of $10^4$–$6·10^5$ ascospores.

* * * * *